(12) United States Patent
Meenink

(10) Patent No.: US 9,060,795 B2
(45) Date of Patent: Jun. 23, 2015

(54) SURGICAL ROBOT, INSTRUMENT MANIPULATOR, COMBINATION OF AN OPERATING TABLE AND A SURGICAL ROBOT, AND MASTER-SLAVE OPERATING SYSTEM

(75) Inventor: Hildebert C. M. Meenink, Steenderen (NL)

(73) Assignee: Technische Universiteit Eindhoven, Eindhoven (NL)

( * ) Notice: Subject to any disclaimer, the term of this patent is extended or adjusted under 35 U.S.C. 154(b) by 126 days.

(21) Appl. No.: 13/499,374

(22) PCT Filed: Oct. 1, 2010

(86) PCT No.: PCT/NL2010/050641
§ 371 (c)(1),
(2), (4) Date: Jun. 17, 2012

(87) PCT Pub. No.: WO2011/040813
PCT Pub. Date: Apr. 7, 2011

(65) Prior Publication Data
US 2012/0245596 A1  Sep. 27, 2012

(30) Foreign Application Priority Data
Oct. 2, 2009  (NL) .................................... 1037348

(51) Int. Cl.
*A61F 9/00* (2006.01)
*A61B 19/00* (2006.01)
*A61B 17/00* (2006.01)
*A61F 9/007* (2006.01)

(52) U.S. Cl.
CPC ... *A61B 19/2203* (2013.01); *A61B 2017/00464* (2013.01); *A61B 2019/2223* (2013.01); *A61B 2019/2234* (2013.01); *A61F 9/007* (2013.01)

(58) Field of Classification Search
CPC ................ A61B 19/2203; A61B 2017/00464; A61B 2019/2211; A61B 2019/2249; A61B 5/15128; A61B 17/00477
USPC .......................... 606/166, 167, 170, 171, 130
See application file for complete search history.

(56) References Cited

U.S. PATENT DOCUMENTS

| 5,435,979 A | 7/1995 | Miller et al. |
| 5,620,456 A * | 4/1997 | Sauer et al. .................... 606/185 |
| 6,451,027 B1 * | 9/2002 | Cooper et al. ................. 606/130 |
| 7,297,142 B2 * | 11/2007 | Brock ................................. 606/1 |
| 2008/0086080 A1 * | 4/2008 | Mastri et al. ............... 604/95.03 |
| 2009/0178943 A1 | 7/2009 | Oostman et al. |

FOREIGN PATENT DOCUMENTS

| WO | WO/2007/133065 | 11/2007 |
| WO | WO/2008/036304 | 3/2008 |

* cited by examiner

*Primary Examiner* — Darwin Erezo
*Assistant Examiner* — Sidharth Kapoor
(74) *Attorney, Agent, or Firm* — Lumen Patent Firm

(57) ABSTRACT

The present invention relates to a surgical robot for performing surgery of the minimally invasive type, comprising an instrument manipulator having a manipulator front end which is provided with an instrument receiver for receiving therein one of a number of surgical instruments, and manipulating means for, at least in use, manipulating the manipulator front end with respect to a patient body. The manipulator front end further comprises a container having a number of container holders for receiving therein the number of surgical instruments, and switching means for switching the instrument present in the instrument receiver by an instrument present in a container holder. The invention further relates to an instrument manipulator, a combination of an operating table and a surgical robot, and a master-slave operating system.

8 Claims, 5 Drawing Sheets

SURGICAL ROBOT, INSTRUMENT MANIPULATOR, COMBINATION OF AN OPERATING TABLE AND A SURGICAL ROBOT, AND MASTER-SLAVE OPERATING SYSTEM

CROSS-REFERENCE TO RELATED APPLICATIONS

This application is a 371 of PCT Patent Application PCT/NL2010/050641 filed Oct. 1, 2010, which claims the benefit of Dutch Application NL1037348 filed Oct. 2, 2009.

DESCRIPTION

The present invention relates to a surgical robot for performing surgery of the minimally invasive type, comprising an instrument manipulator having a manipulator front end which is provided with an instrument receiver for receiving therein one of a number of surgical instruments, and manipulating means for, at least in use manipulating the manipulator front end with respect to a patient body.

The present invention further relates to an instrument manipulator, a combination of an operating table and a surgical robot, and a master-slave operating system.

WO 2008/036304 describes a master-slave operating system. Said operating system for performing ophthalmic microsurgery comprises a tele-robotic master and a slave robot, the slave robot being a surgical robot of the kind mentioned in the introduction, which surgical robot is connected to the master. A medical professional (surgeon) controls manipulation of the slave robot by manually actuating controllers on the master. The slave robot comprises a frame which is connected to a patient table and/or to the patient's head. The slave robot comprises a manipulator front end to which a surgical instrument can be attached, and manipulation means for manipulation of the front end with respect to the patient's head (eye). Multiple slave robots can be used, which can be equipped with various instruments. A disadvantage of the known surgical robot is that switching an instrument of a particular robot is a manually performed, time-consuming and complex procedure, in which the focus of the surgeon is taken away from the point of operation. The object of the present invention is to provide a solution for the above-mentioned problems, or at least an improvement in that regard. In order to achieve that object, the surgical robot according to the invention is characterised in that the manipulator front end further comprises a container having a number of container holders for receiving therein the number of surgical instruments, and switching means for switching the instrument present in the instrument receiver by an instrument present in a container holder. An advantage of the provision of an instrument container in combination with the switching means on the front end of the instrument manipulator is that instruments can be switched automatically, quickly, and that without the need of manipulation of the front end with respect to the patient's body. As a result an instrument can be switched in a safe and quick manner, in which the focus of the surgeon is not taken away from the point of operation.

Although the surgical robot according to the present invention is designed for performing ophthalmic surgery, use of the robot for other (micro)surgical interventions on a human or animal body is included in the scope of the present invention.

Preferably the manipulator front end comprises a base body that can be connected to the manipulating means, wherein the container is moveable with respect to the base body, such that each respective container holder is placeable in alignment with the instrument receiver. In this way switching an instrument is simplified, wherein during an instrument switch the spatial position (with respect to the patient body) of the base body can be fixed, and the container moves with respect to the base body in order to switch an instrument.

It is advantageous if the switching means comprise a guide which is, in a longitudinal direction of the instrument receiver, provided on the manipulator front end, to which guide at least one of the instrument receiver and the container is connected, for moving the container and the instrument receiver towards and away from each other along the guide, in order to switch an instrument between the instrument receiver and a container holder. Due to the presence of said guide allowing relative movement of the instrument receiver and/or the container, an instrument can be switched very easily, since the instrument receiver and the container holder can be brought in direct proximity.

Preferably, the instrument receiver is provided with a passage in a longitudinal direction of the instrument receiver, in which passage an instrument is moveable, whereby the instrument receiver further comprises fixing means for fixing an instrument in the instrument receiver in an active position of the fixing means, and releasing the instrument in a passive position of the fixing means. In this way an instrument can be easily fixed in the instrument receiver by sliding the instrument into the passage of the instrument receiver. In this respect the instrument receiver is preferably elongated and the passage is preferably elongated.

In order to yield a simple though efficient construction, it is preferable if the instrument receiver comprises a sleeve-shaped element in which the passage is provided, and whereby the fixing means comprise a clamp ring which can be translated with respect to the sleeve-shaped element in the longitudinal direction of the sleeve-shaped element, for changing the fixing means from the active position to the passive position and vice versa under the influence of mutual translation of the sleeve-shaped element and the clamp ring.

Preferably, the switching means comprise a stop connected to one of the clamp ring and the sleeve-shaped element, and stop surfaces connected to the other of the clamp ring and the sleeve-shaped element, which stop surfaces are located on both sides of the stop, seen in the direction of mutual translation of the sleeve-shaped element and the clamp ring, and which stop surfaces define the active position and the passive position. In this way the active and passive position can be easily and accurately defined.

Preferably, the stop surfaces form part of a stop element having a first and a second oppositely located crown-shaped body, wherein the first crown-shaped body is circumferentially provided with slots on the side facing the second crown-shaped body, wherein the second crown-shaped body is circumferentially provided with oblique sliding edges on the side facing the first crown-shaped body, which oblique sliding edges form stop surfaces and are located opposite the slots, and wherein the ends of the slots form stop surfaces. Using such crown-shaped bodies, of which oblique sliding edges form stop surfaces on one side of the stop, and of which the ends of slots form stop surfaces at the opposite side of the stop, the active or the passive position can be selected in an easy manner.

In a preferred embodiment the ends of adjacent slots are disposed at alternating positions, seen in the direction of mutual translation of the sleeve-shaped element and the clamp ring, for defining the active position and the passive position. This results in a construction similar to a push button type ballpoint (pen), in which by moving the stop with respect to the stop element, the active position and the passive position are alternatively selected and that in a bistable manner.

A simple construction is obtained if the stop element is formed by a position ring which is rotatable with respect to the sleeve-shaped element and which is provided around the sleeve-shaped element, and that the stop is formed by at least one pin which extends radially from the clamp ring to in between the stop surfaces.

It is advantageous if the switching means comprise a push element located at the top of the instrument receiver, which push element is connected to the clamp ring, which push element translates the clamp ring with respect to the sleeve-shaped element under the influence of mutual translation of the instrument receiver and the container. Due to the push element located at the top of the instrument receiver the clamp ring can be actuated by contacting from below the container with the push element during the mutual translation. This results in a change from the active to the passive position of the fixing means, as a result of which an instrument can be transferred from the instrument receiver to a container holder.

In a constructionally simple embodiment the fixing means comprise a clamp element for fixing the instrument in the instrument receiver under the influence of a clamping force, in the active position. In a preferred embodiment the clamp element comprises a resilient lip, even more preferably a number of lips, preferably three lips, evenly distributed around the perimeter of the passage.

A very simple though efficient construction is yielded if each one of the number of container holders is provided with an opening in which an instrument is moveable, wherein each one of the number of container holders comprises further fixing means for fixing one of the number of instruments in the respective container holder. Preferably the opening is elongated and having its longitudinal direction aligned with the above-mentioned passage of the instrument receiver.

An additional advantage is obtained if the further fixing means comprise a further clamp element for fixing an instrument in the respective container holder under the influence of a further clamping force. A clamp element is a simple solution for efficiently fixing an instrument in a container holder. In a preferred embodiment the further clamp element comprises a resilient lip.

In order to realise a very easy and reliable transfer of an instrument from a instrument receiver to a container holder and vice versa, it is preferable if the clamping force exerted by the further clamp element on an instrument is smaller than the clamping force exerted by the clamp element on the respective instrument. In this way, if an instrument is present in a container holder, during a switch, that instrument just needs to be fixed in the instrument receiver. Next, by moving the instrument receiver away from the container, the instrument is pulled out of the container holder, since the clamping force exerted by the further clamp element on an instrument is smaller than the clamping force exerted by the clamp element on the respective instrument.

In a preferred embodiment the manipulator front did comprises a cannula connection which is aligned with the instrument receiver, and which is, at least in use, positioned on the patient's body and through which an instrument which is present in the instrument receiver is moveable, wherein the manipulator front end further comprises, a guide to which the instrument receiver is connected, for moving the instrument receiver with respect to the manipulator front end along the guide in order to move the instrument through the cannula connection. With such a defined and stiff connection between the cannula and the front end of the instrument manipulator, a very safe switching of instruments can be realised, wherein the focus of the surgeon can be held within the organ of intervention, thereby reducing the chance of error.

The present invention further relates to an instrument manipulator for use in a surgical robot according to the present invention, having a manipulator front end which is provided with a instrument receiver for receiving therein one of a number of surgical instruments, characterized in that the manipulator front end further comprises a container having a number of container holders for receiving therein the number of surgical instruments, and switching means for switching the instrument present in the instrument receiver by an instrument present in a container holder. The advantages that can be achieved with such an instrument manipulator have already been explained in the foregoing in the description of the surgical robot according to the invention.

The present invention still further relates to a combination of an operating table and a surgical robot according to the present invention, wherein preferably the surgical robot is directly connected to the operating table. In this way a very stiff connection between the table and the robot is realised, and the robot can thus be positioned accurately with respect to the patient body, and keep positioned accurately during the surgery.

The present invention still further relates to a master-slave operating system, wherein the slave comprises a surgical robot according to the present invention, and wherein the master is operatively connected to the surgical robot and comprises actuating means for actuating the surgical robot at the distance by a surgeon for, at least in use, performing a surgical treatment to a patient's body.

In such a master-slave operating system, it is preferable if the slave comprises two surgical robots, wherein the actuating means comprise two actuating elements for actuating one of the two respective surgical robots by each respective actuating element. The two actuating elements can be controlled by both hands of the surgeon, by means of which the two robots can be controlled.

The invention will now be explained in more detail by means of a description of a preferred embodiment of the present invention, in which reference is made to the following figures.

Figure 1:
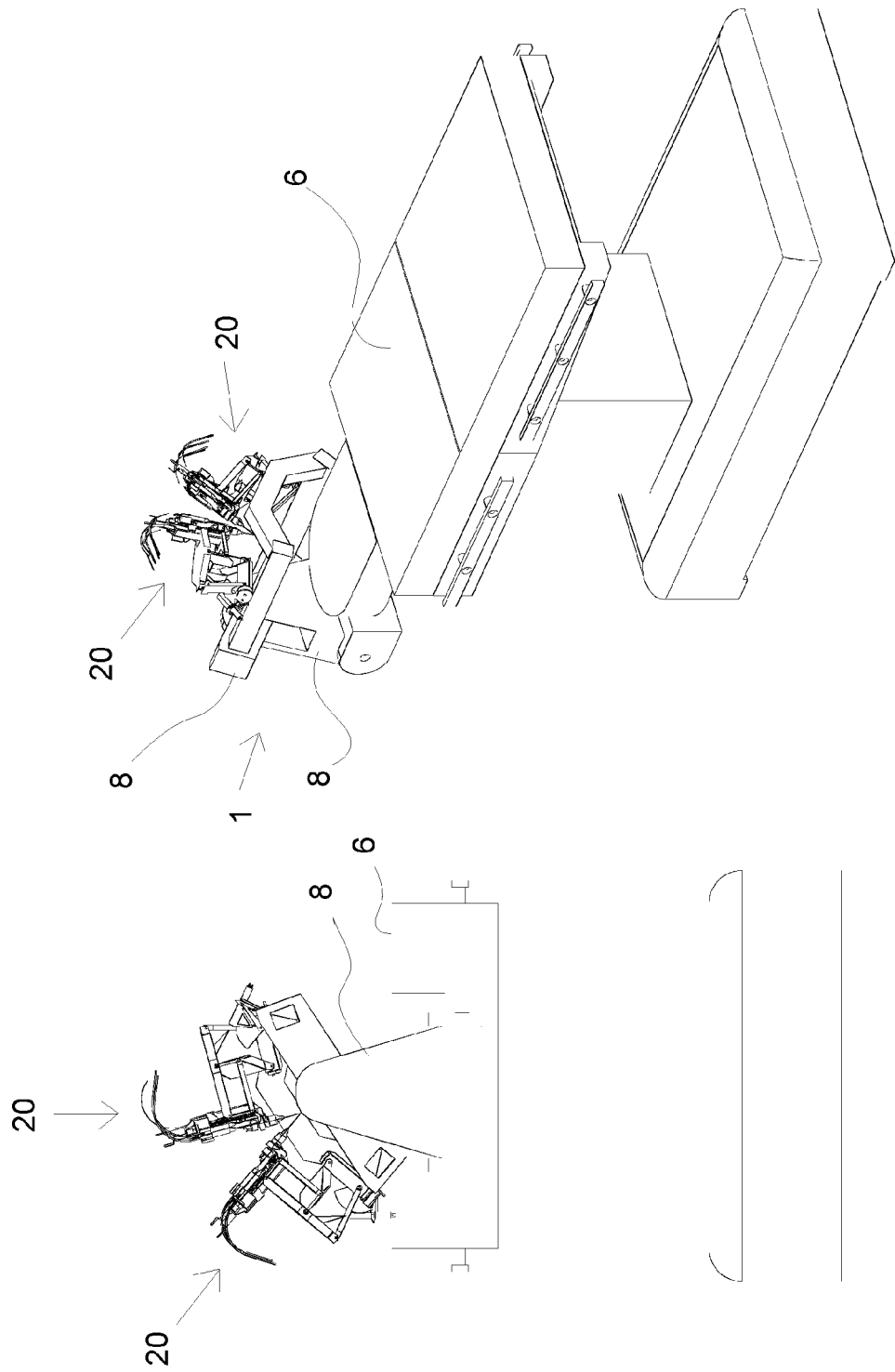
FIGS. 1a and 1b show in front view and in isometric view, respectively, an operating table to which a preferred embodiment of a surgical robot according to the present invention is mounted.

In FIGS. 1a and 1b an operating table 6 is schematically shown. The operating table 6 serves as a support for a patient for ophthalmic microsurgery. A surgical robot system is provided in the operating room in which table 6 is located, comprising a surgical robot 1 acting as a slave robot of a master system (not shown). A surgeon performs the surgery by controlling the motion of the slave robot by manual manipulation of controllers on the master system, whereby the surgical robot 1 performs the actual surgical operation on the patient. A control unit (not shown) is provided which links the master to the robot 1. The control unit comprises motion and force controllers, amplifiers to drive actuators of instrument manipulators 20 of robot 1 as well as hardware safety devices. Furthermore it provides the master-slave robot with haptic properties. Additional perception of the operation can be fed back to the master.

The surgical (slave) robot 1 comprises a supporting frame 8 which is connected to a proximal end of the operating table 6, and two instrument manipulators 20 connected to the frame 8, representing the hands of the surgeon, by which is meant that the surgeon controls the motion of the instruments present on the respective instrument manipulators 20 of the slave robot 1 by manually actuating the controllers on the master system with both his hands. If required more instrument manipulators can be added in order to be able to switch between respective manipulators or to operate on a different region. For relatively simple operations one instead of two instrument manipulators can be provided on the robot 1. Manipulators can for example be added in order to support an endo-illuminator or micro-endoscope. Above the eye of the patient on which the surgery needs to be performed there is room for a light path of a microscope or for the microscope itself.

Figure 2:
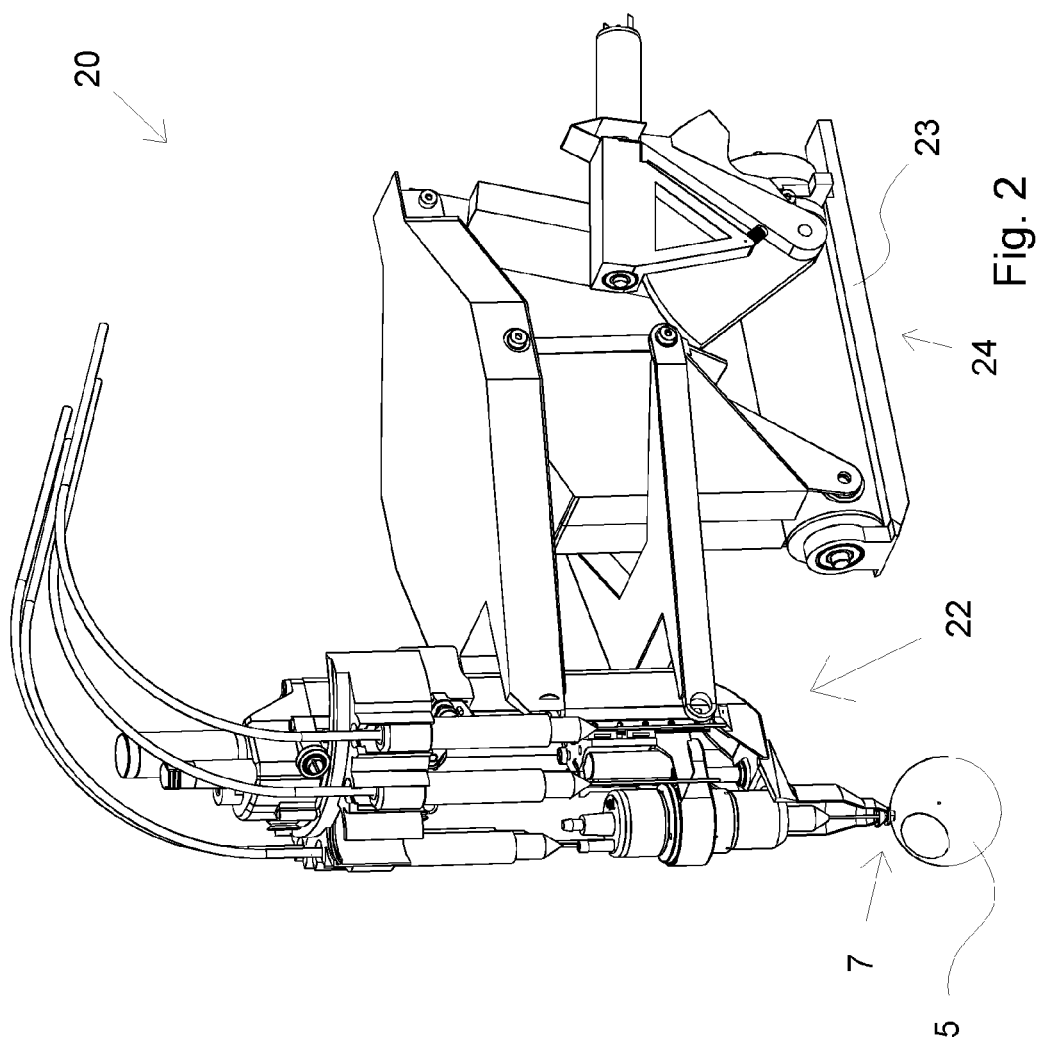
FIG. 2 shows in isometric view an instrument manipulator of the surgical robot according to FIG. 1.

In FIG. 2 an instrument manipulator 20 of the surgical robot 1 is shown in more detail. The instrument manipulator 20 comprises two main parts: a manipulator front end 22 and manipulating means 24. Manipulating means 24 comprise a linkage system which can be manipulated by means of actuators in order to manipulate the manipulator front 22 end with respect to the (eye 5 of the) patient's body. Manipulating means 24 are fixed to the supporting frame 8 by connecting base plate 23 to the supporting frame 8.

The manipulating means 24 are designed such that a remote centre of motion (RCM) is realised at the point of entry into the eye 5. At this centre of motion a cannula 7 is presented, which cannula 7 is fixed at the lower extremity of the front end 22. With such a defined and stiff connection between the cannula and the front end of the instrument manipulator, a very safe switching of instruments can be realised, as will be explained in more detail underneath, wherein the focus of the surgeon can be held within the organ of intervention, thereby reducing the chance of error.

Figure 3:
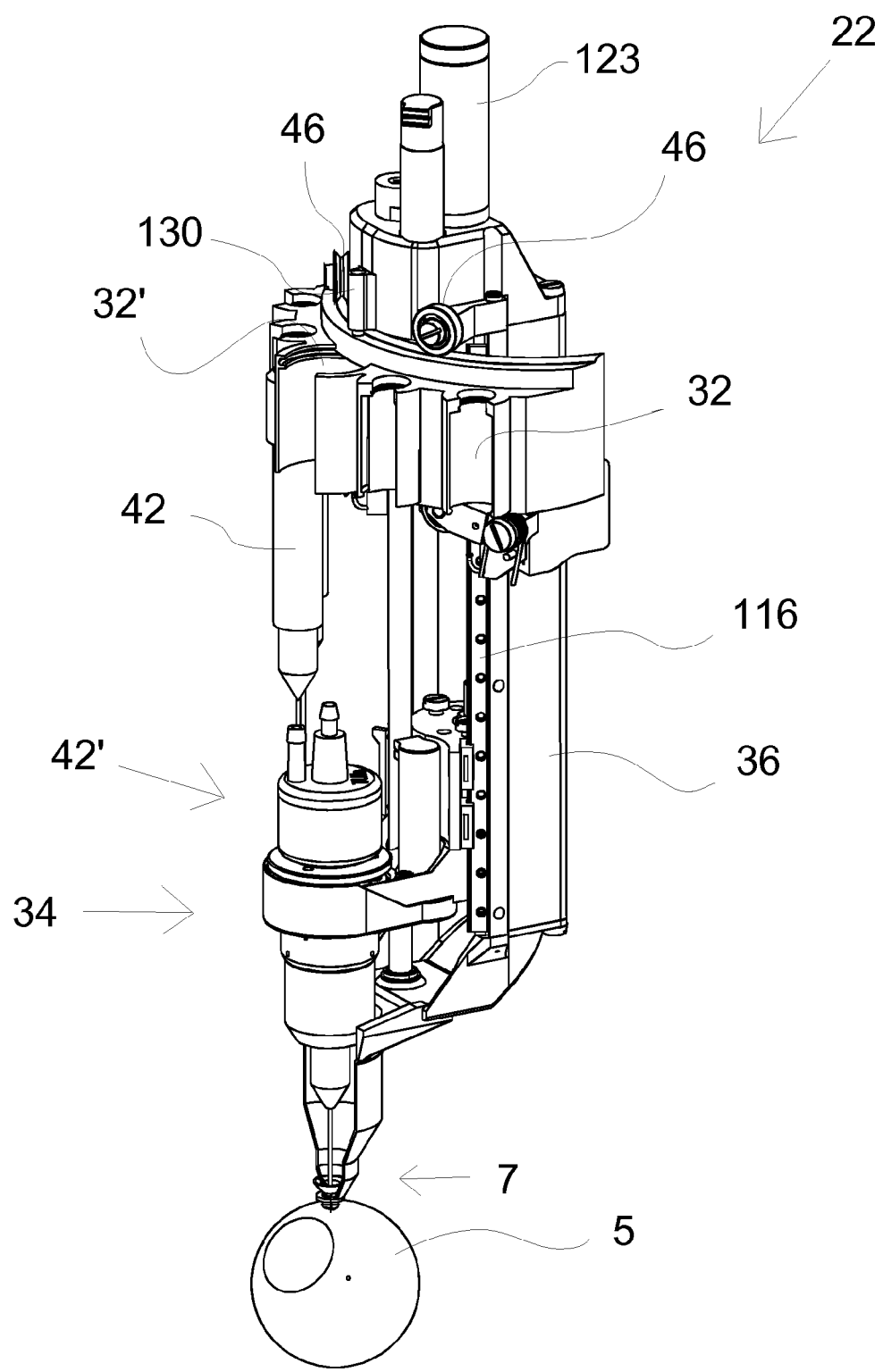
FIG. 3 shows in isometric view the manipulator front end of the instrument manipulator of FIG. 2.
Figure 4:
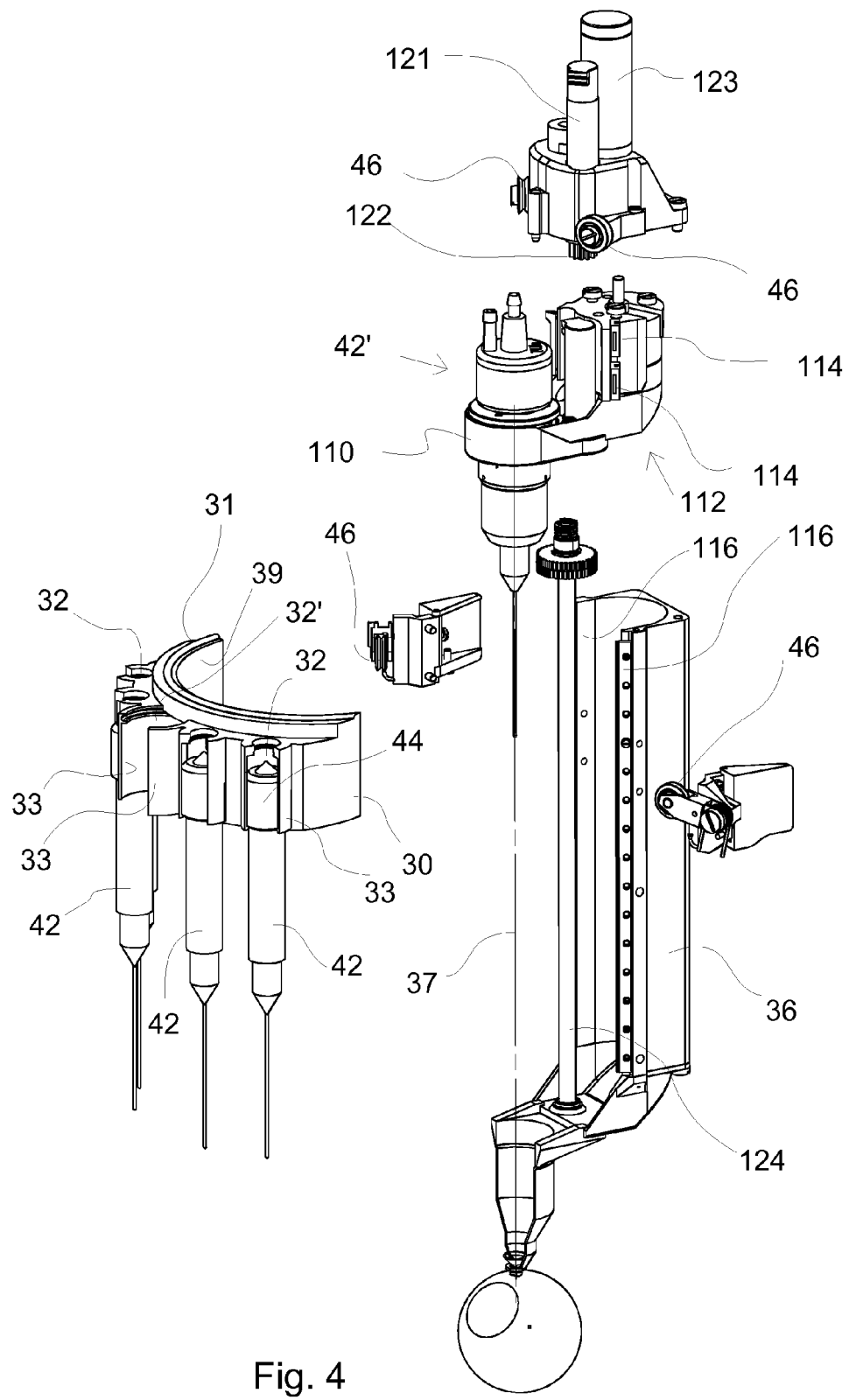
FIG. 4 shows in isometric view the manipulator front end of FIG. 3 in exploded view.

FIG. 3 shows the manipulator front end 22 of the instrument manipulator 20 in more detail. In FIG. 4 the front end 22 is shown in exploded view. In FIG. 3 with respect to FIG. 4 two less instruments 42 are shown for clarity purposes. The front end 22 comprises a base body 36 on which an instrument receiver 34 for a surgical instrument 42, 42' is movably, along the longitudinal direction of base body 36, provided. Furthermore an instrument container 30 is provided which can be rotated with respect to the longitudinal direction of base body 36, which longitudinal direction is displayed by means of dashed line 37 in FIG. 4. Base body 36 is directly fixed to the manipulating means 24.

Instrument container 30 is part-cylindrical shaped and includes five container holders 32, 32' for receiving therein four surgical instruments 42 and one surgical instrument 42'. Container 30 is provided with a guide 31 on an upper end face as well as on a lower end face (not shown), over which guide 31 rollers 46 having a circumferential groove which is adapted to the shape of guide 31 are provided, which rollers are connected to base body 36. Container 30 is movable with respect to the base body 36 by actuating motor 121. Motor 121 is operatively connected via a gear 122 to a gearing (not shown) present on back surface 39 of container 30. As an alternative for mentioned motor 121 and gear 122, at least one of the rollers 46 can be driven in order to rotate container 30 with respect to base body 36. Container holders 32, 32' are provided along an outer surface of container 30. The respective holders 32, 32' are each bounded by two resilient wall parts 33 which define a cylindrical passage and which act as leaf springs for clamping a surgical instrument 42, 42' in a respective container holder 32, 32'. The instrument container 30 as shown in FIG. 3 has four container holders 32 for receiving therein four respective instruments 42 and has one container holder 32' for receiving therein one instrument 42'. Obviously other numbers of container holders 32, 32' and different shaped container holders can be provided on the instrument container 30, depending on the number of different instruments used during the operation and the specific geometry of the instruments used. Instrument container 30 can be provided together with instruments in one sterile sealed package, wherein the container can be mounted on the instrument manipulator just before the surgical operation. Furthermore the overall shape of the container 30 can be part-cylindrical, fully cylindrical, or more or less straight.

For facilitating a very easy mounting of a, container, whether or not already including instruments, on the base body 36, two rollers 46 which are located at the bottom side of the container (at least when mounted) are provided on arms that are pivotably connected to base body 36. Using springs located at the pivots of the mentioned arms, the rollers 46 are urged upwards due to the spring force. Two rollers 46 that are located at the upper side of container 30 (at least when mounted) are rotatably connected to base body 36 but cannot move with respect to base body 36. In order to mount a container 30, the two lower rollers can manually be pivoted downwards against the force of the springs such, that space is provided for fitting container 30 with its two guides 31 in mentioned space. After positioning the container in between the four rollers 46, the arms of the two lower rollers can be released thus the two lower rollers then engage the lower guide 31 of the container 30. Mentioned springs provide a tensioning of lower rollers 46 against lower guide 31 which consequently forces upper guide 31 against upper rollers 46 and thus realizes a stable and well-defined connection between container 30 and base body 36.

Surgical instruments 42 are at least partly cylindrical-shaped and are provided with an upper cylindrical part 44 of which the diameter is adapted to the inner surfaces of resilient wall parts 33 of a container holder 32. In the embodiment shown in FIG. 4, four surgical instruments 42 are identically shaped, at least regarding their upper part, and one surgical instrument 42' has an upper part 44' having a larger diameter. Therefore container holder 32' also has a larger dimension compared to the container holders 32. Surgical instruments 42, 42' all have a lower cylindrical section having a specific diameter in order to make all instruments 42, 42' fit in the instrument receiver 34, as will be explained below.

Container holders 32, 32' are shaped such that an instrument 42, 42' is movable therein in vertical direction (along the longitudinal direction 37 of base body 36). In order to mount an instrument 42, 42' in one of the respective container holders 32, 32' the respective instrument is slided from below the respective container holder 32, 32' in upward direction until the clamping force between upper section 44, 44' of instrument 42, 42' and resilient wall parts 33 is such that the instrument 42, 42' remains fixed in the respective container holder 32, 32'. For increasing smooth entering of an instrument 42, 42' into a holder 32, 32' an upper edge of the upper part 44, 44' of the instruments is made slightly conical. In order to minimize the risk of accidental sliding of an instrument out of a holder 32, 32', the bottom edge of each wall part 33 of the respective holders is provided with a small inwardly extending rib, engaging just under the lower edge of the upper part 44, 44' of the instruments 42, 42', when the instrument is fully slided into a holder 32, 32'. An instrument to be selected for surgery can be positioned directly above (in alignment with) the instrument receiver 34 by actuating rollers 46 as explained above. Instrument selection by rotation of container 30 thus takes place in a revolver-like way.

Instrument receiver 34 is connected to base body 36 by means of a connector piece comprising a cylindrical part 110 and a guide part 112, which guide part 112 is provided with guide shoes 114 by means of which the connector piece and thus the instrument receiver 34 can slide in up- and downward direction along guides 116 on base body 36. In order to accurately control movement of the instrument receiver 34 along mentioned guide 116 a motor 123 present on base body 36 can be driven, which motor 123 is, via gears, connected to a schematically shown spindle 124, the gearing on which spindle meshes with a gearing (not shown) present in the guide part 112 of instrument receiver 34.

Figures 5A, 5B:
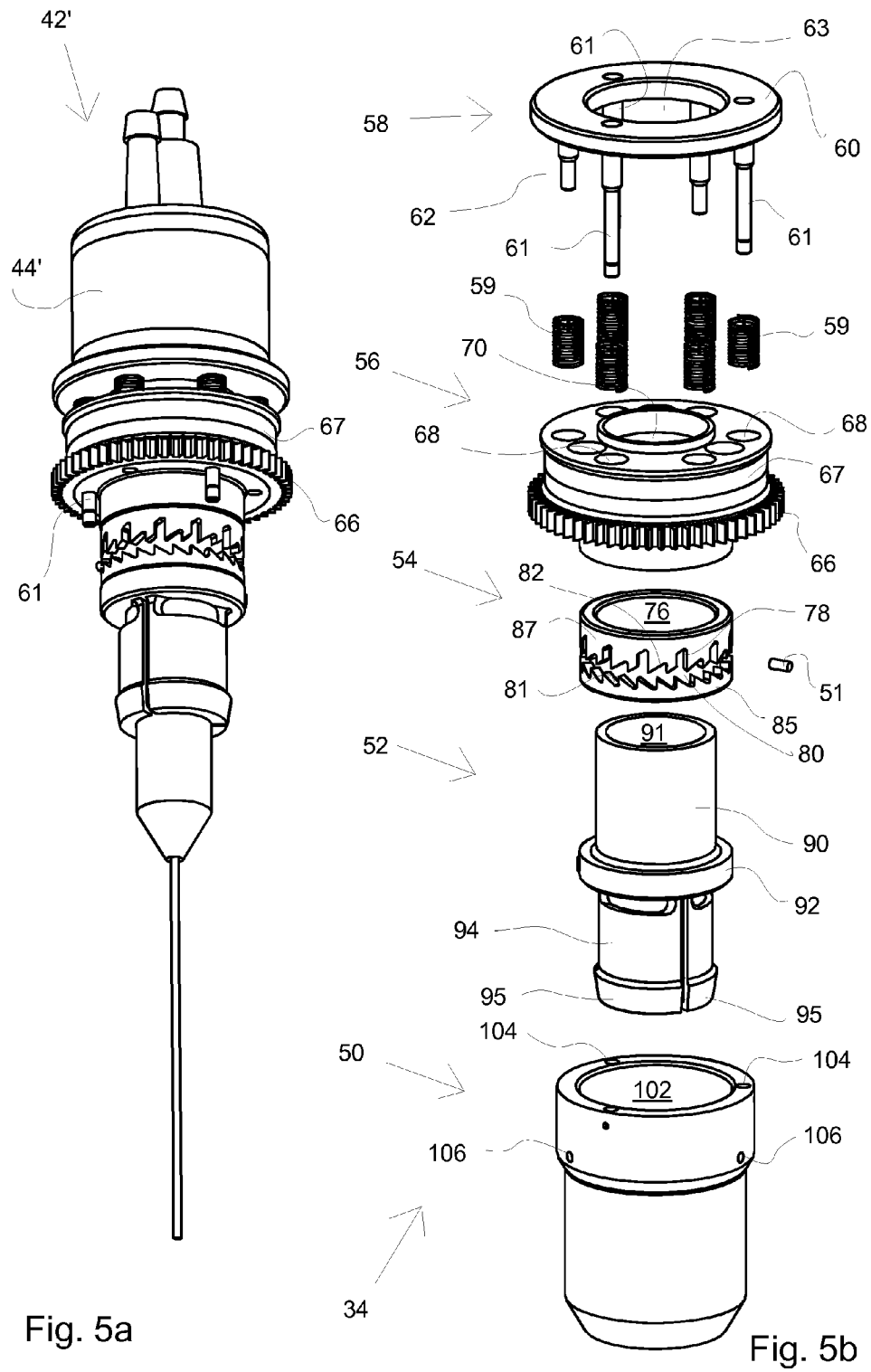
FIGS. 5a and 5b show in isometric and exploded view, respectively, the instrument receiver of the manipulator front end according to FIG. 3.

Cylindrical part 110 is provided with a rotational guide which engages side wall 67 of connector ring 56 (see FIGS. 5a and 5b). The mentioned rotational guide thus enables the connector ring 56 and thus the instrument present in the instrument receiver 34, as will be explained underneath, to rotate around its longitudinal axis 37, while the rotational guide blocks any other degree of freedom of ring 56. Within cylindrical part 110, furthermore driving means are present which engage gear 66 of connector ring 56 by means of which the rotation of instrument receiver 34 it can be controlled. Thus, instrument receiver 34 can be rotated around its longitudinal axis 37 as well as translated with respect to base body 36 along said longitudinal axis 37.

FIGS. 5a and 5b show instrument receiver 34. Clamp ring 50 as shown in FIG. 5b is not shown in FIG. 5a for clarity purposes. An instrument to be fixed in the instrument receiver 34 can be translated downwards from above instrument receiver 34 into the instrument receiver 34, whereby the instrument moves downwards through bore 63 of push ring 58, through bore 70 of connector ring 56, and into bore 91 of sleeve 52, which bore 91 has a diameter which is adapted to the outer diameter of a lower cylindrical part of a specific instrument 42, 42'.

In assembled state of the instrument receiver 34 three downward extending pins 61 of push ring 58 extend through bores 68 of connector ring 56 and are fixed into holes 104 of clamp ring 50, thus realizing an assembly of push ring 58 and clamp ring 50. Around pins 61 helical springs 59 are present, acting between connector ring 56 and push ring 58. Push ring 58 furthermore comprises further pins 62 which extend into further bores in connector ring 56. Mentioned further pins 62 are in fact only present to keep the further springs 59 positioned, which further springs 59 act between connector ring 56 and push ring 58 and serve in order to increase the spring force in between rings 58 and 56. Each one of the springs 59 thus acts between connector ring 56 and push ring 58. Connector ring 56 and positioning ring 54 slide over outer surface 90 of sleeve 52, whereby the lower end face of positioning ring 54 comes to rest against shoulder 92 of sleeve 52. Although positioning ring 54 is in assembled state locked in vertical direction between shoulder 92 of sleeve 52 and connector ring 56, positioning ring 54 can rotate freely around cylindrical part 90 of sleeve 52. Clamp ring 50 slides with an inner surface of bore 102 over the outer diameter of shoulder 92 and comprises three radial pins 51 that are fixed in holes 106, which pins 51 extend into bore 102 and in an assembled state extend into the groove 80 of positioning ring 54. Bore 102 of clamp ring 50 has a tapered section at its lower side which, at least at assembled state of instrument receiver 34, can engage tapered faces 95 of three resilient lips 94 as will be explained below, which lips 94 are equally distributed provided on the perimeter of the lower end face of shoulder 92 of sleeve 52.

Due to helical springs 59, which are present around pins 61 and 62 and act in between push ring 58 and connector ring 56, the push ring 58 together with the clamp ring 50 (due to pins 61 which connect ring 58 with ring 50) is forced upwards with respect to the assembly of connector ring 56, positioning ring 54 and sleeve 52. The inner tapered section of clamp ring 50 then forces the resilient lips 94 to move radially inwards due to the force exerted by helical springs 59 and thus, at least if an instrument is present in sleeve 52, resilient lips 94 radially clamp and thereby fix the instrument in instrument receiver 34. If push ring 58 on the other hand is pushed downwards (against the direction of the force exerted by springs 59) with respect to sleeve 52, the inner tapered section of clamp ring 50 disengages from tapered sections 95 of resilient lips 94 which leads to a release of the instrument clamped in sleeve 52 since the radial clamping force exerted by lips 94 on the instrument is lost.

The special shape of the groove 80 on the outer surface of positioning ring 54 leads to a bistable clamping behaviour of instrument receiver 34, as will be explained now. Positioning ring 54 has two facing crown-shaped body parts 85, 87 mutually connected by a cylindrical inner wall part. Groove 80 is thus present in between said crown-shaped body parts 85 and 87. Body part 85 is circumferentially provided with oblique sliding edges 81, like sawteeth, on its side facing body part 87. Body part 87 is circumferentially provided with slots on its side facing body part 85. Oblique sliding edges 81 as well as the ends 78, 82 of the respective slots form stop surfaces for pins 51. The slots having ends 78 are relatively longer than the slots having ends 82 thus the stop surfaces defined by the ends 78 are located further from the opposite sliding edges 81 than the stop surfaces defined by the ends 82. Slots having ends 78 and 82, respectively, are provided in an alternating manner around the perimeter of positioning ring 54. Opposite each slot a sliding edge 81 is present. Pins 51 come to rest against one of the oblique sliding edges 81 of groove 80 each time push ring 58 and thus clamp ring 50 is pushed downwards with respect to sleeve 52 and thus also with respect to positioning ring 54. Due to the sliding along an oblique sliding edge 81 by each of the respective pins 51 during the downward movement of pins 51, positioning ring 54 rotates with respect to pins 51 over the length of one edge 81. In order to be complete it is mentioned that rotation of clamp ring 52 around axis 37 is prevented by pins 61 extending through bores 68 of connector ring 56. Rotation of connector ring 56 is, as mentioned, controlled by actuation of gear 66, which rotation of ring 56 is blocked during an instrument switch. When push ring 58 is then released, the force exerted by springs 59 pushes the push ring 58 upwards with respect to sleeve 52 and pins 51 move upwards in groove 80 and come to rest against either an end 78 or an end 82. Consequently each time a downward and upward movement of clamp ring 50 with respect to positioning ring 54 is effected, pins 51 end up alternately in one of the slots having ends 78 or 82. This principle can generally be compared to the known principle of the push button type ballpoint (pen).

Pins 51 either resting against the end 78 or 82 control the ability to clamp an instrument in sleeve 52. When pins 51 are present against an end 78, clamp ring 50 can move upwards with respect to sleeve 52 over such a distance that an instrument can be clamped by the inward motion of resilient lips 94. On the other hand, when radial pins 51 move vertical against an end 82, upward movement of clamp ring 50 with respect to sleeve 52 is limited such that no radial inward force is exerted by resilient lips 94 on an instrument present within sleeve 52. The advantage of such a bistable behaviour of instrument receiver 34 will now be explained by describing an instrument switching operation.

If the instrument 42' as shown in FIG. 3 needs to be switched by one of the instruments 42 as shown in FIG. 3, at first, if not already present above instrument receiver 34, the empty container holder 32' is positioned directly above (aligned with) the instrument receiver 34 by a rotation of the instrument container 30 with respect to base body 36 as described above. Next, instrument receiver 34 is translated upwards along guides 116 until upper section 44' of instrument 42' enters container holder 32' of instrument container 30 from below. The clamping force exerted by resilient walls 33 of container holder 32' is such that the instrument receiver is still able to translate in vertical direction while upper section 44' slides further into instrument holder 32'. In other words, the clamping force exerted by walls 33 on the instrument is lower than the clamping force exerted by lips 94 on the instrument. When moving further upwards, the upper end face 60 of push ring 58 comes into contact with the lower end face of container holder 32'. When moving even further upwards, push ring 58 moves downwards with respect to sleeve 52 against the force exerted by springs 59, which leads to a downward motion of clamp ring 50 with respect to sleeve 52, thus releasing the instrument 42' from sleeve 52. The clamping force by walls 33 now effects fixation of the instrument 42' in holder 32'. During this downward motion of clamp ring 50 with respect to sleeve 52, pins 51 move downwards from a slot having an end 78 in the direction of the oppositely present edge 81 and positioning ring 54 rotates over one index position due to sliding of pins 51 over one length of an edge 81, as explained above. When the instrument receiver 34 is then moved downwards again, due to the rotated position of positioning ring 54, during this downward movement radial pins 51 come to rest against a stop surface of the adjacent slot, having an end 82, resulting in a limitation of upward movement of clamp ring 50 with respect to sleeve 52 and thereby prevention of effecting a radial inward force on the instrument by resilient lips 94. Thus, instrument receiver 34 moves downward while instrument 42' then stays clamped in container holder 32'.

When instrument receiver 34 is moved downwards over a sufficient distance (meaning until instrument receiver 34 is completely out of range of instrument 42'), instrument container 30 is rotated such that the desired instrument 42 comes to lie directly above instrument receiver 34. Then instrument receiver 34 moves upwards again until upper end face 60 of push ring 58 contacts a lower end face of the respective container holder 32. At this time the instrument 42 has slided into sleeve 52. During this upward action, analog as described above, push ring 58 is moved downwards with respect to sleeve 52 and consequently radial pins 51 index one position further with respect to positioning ring 54. When the instrument receiver 34 is moved downwards again, radial pins 51 become bounded at the relatively higher location of an end 78 in a slot of positioning ring 54, as a result of which clamp ring 50 is able to move over such a distance upwards with respect to sleeve 52 that clamp ring 50 can effect radial inward force on resilient lips 94 which lead to a firm clamping engagement of the instrument 42 within sleeve 52. Downward movement of instrument receiver 34 pulls the instrument 42 out of the container holder 32 since the clamping force by the lips 94 is higher than the clamping force by walls 33, including locking force effected by the above-mentioned rib present on walls 33. The switched instrument 42 can now be moved (further) downwards into the eye of the patient and the surgery can continue. A switching operation as described above proceeds fully automated and in practice takes a few seconds.

As a precautionary measure movement (rotation) of container 30 with respect to base body 36 is prevented in case an instrument is pulled out of that one of the container holders 32, 32' that is positioned in line with the instrument receiver 34. To realise this a locking element is provided acting between the container holder 30 and the base body 36, comprising a spring-tensioned pin 130 that is provided on base body 36, which pin 130 engages a flat upper surface of container 30. Mentioned upper surface comprises pawl-shaped inserts, present at the location of each one of the container holders 32, 32'. The inserts have an upper end which is flat and coplanar with the upper surface, at least in case an instrument is present in the respective container holder. In case instruments are present in each one of the container holders 32, 32' thus a flat path is realized over which path pin 130 can slide and container 30 thus can rotate with respect to base body 36. In case during an instrument switch an instrument is however pulled out of a container holder, as described above, the pawl drops down over a pre-determined distance into a thereto provided space in the material of container 30, thereby creating a hole in the upper surface of container 30. As a result of this, the pin 130, which is located directly above mentioned pawl, is urged into the hole created by the pawl and thus blocks rotation of the container 30 with respect to base body 36. In case an instrument is pushed back into a container holder as described above, the pawl is urged upwards again until its upper end is coplanar with the upper surface of container 30, thereby restoring the path over which pin 130 can slide and thereby thus releasing the locking between container 30 and base body 36. Using mentioned pin 130 in combination with pawl-shaped inserts a very accurate locking is provided which takes places automatically, meaning no operator action is required. This results in an increased safety level during instrument switches.

The invention claimed is:

1. A surgical robot for performing a medical procedure, comprising:
    (a) an instrument manipulator comprising a manipulator front end, wherein said manipulator front end comprises a base body defining a longitudinal axis with a proximal end and a distal end;
    (b) a container movably connected to said base body near said proximal end of said longitudinal axis, wherein said container comprises a plurality of instrument holders each for holding a surgical instrument, wherein each of said instrument holders has a through-hole for holding said surgical instrument, wherein said through-hole has a proximal end and a distal end in the direction of said longitudinal axis, and wherein at least part of said surgical instrument when held in said instrument holder extends passed said distal end of said through-hole and towards said distal end of said base body;
    (c) an instrument receiver for receiving done of said surgical instruments from below said distal end of said respective through-hole of said instrument holder, wherein said instrument receiver comprises a clamping mechanism, wherein said clamping mechanism can clamp said surgical instrument when said clamping mechanism is changing from a passive no-clamping state to an active clamping state;
    (d) a cannula connector with a proximal end and a distal end both aligned with said longitudinal axis of said base body, said cannula connector is a rigid connector mounted to said distal end of said base body, said cannula connector receiving said surgical instrument to go through said cannula connector, wherein said cannula connector remains distal to said instrument receiver and is aligned with said longitudinal axis of said instrument receiver, wherein said cannula connector can be fixated onto a cannula to establish a connection between said base body and said cannula via said cannula connector, wherein said cannula is also aligned with said longitudinal axis;

(e) a linear guide to actively guide said instrument receiver towards said instrument holder where said instrument receiver can actively clamp said surgical instrument through said clamping mechanism, wherein said linear guide can actively guide said instrument receiver with said clamped surgical instrument in longitudinal direction towards said cannula connector, and wherein the translation of said instrument receiver towards said cannula connector while said surgical instrument is clamped by said clamping mechanism of said instrument receiver causes said surgical instrument to be released from said instrument holder; and (f) a switching mechanism for switching said surgical instruments along said longitudinal axis and between one of said instrument holders and said instrument receiver, whereby said container if applicable rotates to align one of said instrument holders with said instrument receiver.

2. The surgical robot as set forth in claim 1, wherein said cannula can be fixated onto a human or an animal body.

3. The surgical robot as set forth in claim 2, wherein said human or animal body is an eye.

4. The surgical robot as set forth in claim 2, wherein a spatial position between said base body and said human or animal body is fixed when switching one of said surgical instruments.

5. The surgical robot as set forth in claim 1, wherein said through-hole is at least part cylindrical.

6. The surgical robot as set forth in claim 1, wherein said container rotation is in a plane perpendicular to said longitudinal axis.

7. The surgical robot as set forth in claim 1, wherein said surgical robot is part of a master-slave operating system.

8. The surgical robot as set forth in claim 1, wherein the inner diameter of said cannula connector changes over the length of said cannula connector between said proximal and distal ends.

* * * * *